(12) United States Patent
Chu et al.

(10) Patent No.: US 9,186,090 B2
(45) Date of Patent: Nov. 17, 2015

(54) METHOD AND SYSTEM FOR DLCO QUALITY CONTROL TESTING

(71) Applicant: nSpire Health, Inc., Longmont, CA (US)

(72) Inventors: Edmond Chu, Erie, CO (US); Eric Norgard, Louisville, CO (US); William Chase Wallace, Johnstown, CO (US)

(73) Assignee: nSpire Health, Inc., Longmont, CO (US)

( * ) Notice: Subject to any disclaimer, the term of this patent is extended or adjusted under 35 U.S.C. 154(b) by 230 days.

(21) Appl. No.: 13/682,199

(22) Filed: Nov. 20, 2012

(65) Prior Publication Data

US 2014/0142454 A1   May 22, 2014

(51) Int. Cl.
| | |
|---|---|
| *G01M 3/00* | (2006.01) |
| *A61B 5/08* | (2006.01) |
| *G01N 33/497* | (2006.01) |
| *A61B 5/097* | (2006.01) |

(52) U.S. Cl.
CPC .............. *A61B 5/082* (2013.01); *G01N 33/497* (2013.01); *A61B 5/0813* (2013.01); *A61B 5/097* (2013.01)

(58) Field of Classification Search
CPC ..... G01M 3/02; G01M 99/007; A61F 2/2472; G01N 3/32; A61B 19/46; A61B 5/082
USPC ................................................ 73/37; 600/532
See application file for complete search history.

(56) References Cited

U.S. PATENT DOCUMENTS

| | | | | |
|---|---|---|---|---|
| 4,083,367 | A * | 4/1978 | Portner et al. ................ | 600/504 |
| 5,022,406 | A * | 6/1991 | Tomlinson .................... | 600/532 |
| 5,193,551 | A * | 3/1993 | Pilipski ......................... | 600/529 |
| 6,415,642 | B1 * | 7/2002 | Crapo et al. ................... | 73/1.05 |
| 2009/0038371 | A1 * | 2/2009 | Verbraak et al. ............... | 73/1.06 |

* cited by examiner

*Primary Examiner* — Peter Macchiarolo
*Assistant Examiner* — Mohammed Keramet-Amircola
(74) *Attorney, Agent, or Firm* — Cooley LLP

(57) ABSTRACT

The present invention can provide a system and method for $D_{LCO}$ quality control testing and can include an apparatus for testing a pulmonary diagnostic device capable of performing single breath carbon monoxide uptake measurement, comprising: a single gas-tight chamber, with a gas port configured to receive gas from or to expel gas to the exterior of the chamber and a partition configured to change the volume of the single gas-tight chamber; the single gas-tight chamber capable of expanding and contracting; a member disposed within the single gas-tight chamber and configured to limit the movement of the partition, the member being adjustable to set a predetermined maximum volume of the single gas-tight chamber and a predetermined volume of $D_{LCO}$ test gas that the single gas-tight chamber can receive; and an interface configured for the transfer of gas between the pulmonary diagnostic device and the simulation device via the gas port.

13 Claims, 10 Drawing Sheets

METHOD AND SYSTEM FOR DLCO QUALITY CONTROL TESTING

COPYRIGHT

A portion of the disclosure of this patent document contains material that is subject to copyright protection. The copyright owner has no objection to the facsimile reproduction by anyone of the patent disclosure, as it appears in the Patent and Trademark Office patent files or records, but otherwise reserves all copyright rights whatsoever.

FIELD OF THE INVENTION

The present invention relates to quality control of $D_{LCO}$ equipment. In particular, but not by way of limitation, the present invention relates to systems and methods for ensuring the measurement accuracy of pulmonary testing devices used for single-breath determination of carbon monoxide uptake in the lung.

BACKGROUND OF THE INVENTION

Current $D_{LCO}$ simulators require large and expensive dual-syringe devices. For example, the Hans Rudolph $D_{LCO}$ simulator, as described in U.S. Pat. No. 6,415,642 requires two syringes (3 and 5 liters) that are joined by a manifold via a three-way valve. The manifold is connected to the $D_{LCO}$ equipment. Prior to the start of the simulation test, the 3-liter syringe is filled with a precision gas mixture emulating typical alveolar gas concentration seen in patients. Using the three-way valve, the 5-liter is connected to the $D_{LCO}$ equipment while the 3-liter syringe is isolated with the prefilled precision gas mixture. During the inhalation phase of the $D_{LCO}$ test maneuver, the 5 liter syringe simulates tidal breathing, exhalation to residual volume, and rapid inhalation to TLC. During the breath hold period, the 3-way valve is turned redirecting the $D_{LCO}$ device to the 3 liter syringe. After the breath hold, the content of the 3-liter syringe is emptied into the $D_{LCO}$ device.

The Hans Rudolph simulator "establishes" approximate target $D_{LCO}$ values for the $D_{LCO}$ device under test by controlling the inspired volume as well as the inspired and alveolar gas concentrations. To verify equipment performance over its specified range of operation, it requires multiple precision alveolar gas mixtures with different concentrations of CO and tracer gases.

Because the Hans Rudolph does not control the breath hold time, the breath hold time reported by the $D_{LCO}$ device under test is required to confirm the exact target value. Hans Rudolph provides software for the calculation of the exact target value (based on Eq (1)) after the test is performed.

For trouble-shooting, ATS-ERS (MacIntyre N. et. al. Standardization of the single-breath determination of carbon monoxide uptake in the lung. Eur Respir J 2005; 26: 720-735) also recommends the following:
1. Leak testing if it is appropriate to the device under test
2. A $D_{LCO}$ test with a calibrated 3.0-L syringe should be used, which is performed by attaching the syringe to the instrument in the test mode. Test gas is withdrawn from the $D_{LCO}$ machine by the syringe and then reinserted at the end of the breath-hold. The measured $D_{LCO}$ should be near zero and the measured VI should be ≈3.3 L (3.0 L×the body temperature, ambient pressure, saturated with water vapor (BTPS) factor). This procedure checks the inhaled volume accuracy in the $D_{LCO}$ test mode, which may be in error when spirometry measurements are not.

The simulator identified in the ATS-ERS $D_{LCO}$ testing guideline (MacIntyre N. et. al. Standardization of the single-breath determination of carbon monoxide uptake in the lung. Eur Respir J 2005; 26: 720-735) was developed by Glissmeyer, et. al. (Glissmeyer E W, Jensen R L, Crapo R O, Greenway L W. Initial Testing with a carbon monoxide diffusing capacity simulator. J Invest Med 1999; 47: 37A) and manufactured by Hans Rudolph, Inc, Kansas City, Mo.

Current $D_{LCO}$ testing devices and practices suffer from several deficiencies and disadvantages. The trouble-shooting methodology suggested by ATS-ERS (using a 3 liter syringe) does not affirm the $D_{LCO}$ measurement accuracy of a $D_{LCO}$ device over its intended range of operation. At best, this test establishes the accuracy of flow/volume measurement component of the $D_{LCO}$ device. It may also demonstrate that the CO and tracer gas detectors have similar response (but not necessarily accurate or linear) over a narrow range of gas concentrations.

The use of the Hans Rudolph simulator for quality control of $D_{LCO}$ measurements has been well documented (Jensen R, et. al. Quality control of $D_{LCO}$ instruments in global clinical trials. Eur Respir J 2009; 33: 1-7. Jensen R L, et. al. Instrument Accuracy and Reproducibility in Measurements of Pulmonary Function. Chest 2007; 132: 388-395.).

There are a number of challenges and disadvantages in using the Hans Rudolph simulator. First, the procedure is complex and prone to errors. The 3-liter syringe used to simulate exhalation must be filled with precisely known concentration of alveolar gas prior to each test. The syringe must be adequately purged prior to filling. Difficulties arise from a significant certainty that the syringe is properly purged of any previously used gas mixtures. Moreover, during the testing process, the 3-way valve must be turned immediately before the emptying of the 3-liter syringe begins to ensure any chance that the test is accurate. If precise timing of the operation of the 3-liter syringe is not maintained the test of the $D_{LCO}$ equipment is invalid and the test must be re-performed, resulting in increased costs for the precise gas mixtures used in the testing or even improper calibration of the $D_{LCO}$ equipment based on faulty test results.

Second, target $D_{LCO}$ value changes with every test and every new gas cylinder. To ensure that $D_{LCO}$ device operates correctly throughout its intended range of operation, it must be tested at various combinations of CO and tracer gas concentrations, thereby requiring a number of precision (typically 1% or better) pre-mixed gases. Switching alveolar gas bottles adds to the complexity and cumbersomeness of simulator testing.

Third, precision gases are expensive. Delivery and shipment of the precision gases are difficult as these gases are typically classified as medical gases by many countries. One purpose of $D_{LCO}$ equipment is to perform clinical studies or trials in remote locations. For studies and trials to have statistically valid results, the $D_{LCO}$ equipment, which may be in multiple remote locations, must be properly calibrated. This calibration of multiple, remote $D_{LCO}$ equipment simulators is complex in and of itself and even more so with the added cost and complexity of shipping the required medical gases used in the testing.

Fourth, the current $D_{LCO}$ simulators, even though a fraction of the cost of the $D_{LCO}$ device, is relatively expensive. Current simulators require their own test gas which can be costly Fifth, current simulators are bulky, which also adds to their cost. They require two syringes along with precision test gases. As discussed above, shipping and other costs for current simulators are high not only because of the required precision gases, but costs can increase for storage of the simulator and the gases it requires. All of these costs are exacerbated considering that many times $D_{LCO}$ equipment is used in remote and often poor locations and for non-profit endeavors, such as clinical studies or trials.

Although present devices are functional, they are not sufficiently accurate or otherwise satisfactory. Accordingly, a system and method are needed to address the shortfalls of present technology and to provide other new and innovative features.

SUMMARY OF THE INVENTION

Exemplary embodiments of the present invention that are shown in the drawings are summarized below. These and other embodiments are more fully described in the Detailed Description section. It is to be understood, however, that there is no intention to limit the invention to the forms described in this Summary of the Invention or in the Detailed Description. One skilled in the art can recognize that there are numerous modifications, equivalents and alternative constructions that fall within the spirit and scope of the invention as expressed in the claims.

The present invention can provide a system and method for $D_{LCO}$ quality control testing. In one exemplary embodiment, the present invention can include a method for testing a pulmonary diagnostic device comprising: accepting a first configured predetermined maximum volume of a space; receiving atmospheric gas into the space; receiving a predetermined volume of a first $D_{LCO}$ test gas from the pulmonary diagnostic device into the space, the first configured predetermined maximum volume being larger than the predetermined volume of the first $D_{LCO}$ test gas, the first $D_{LCO}$ test gas comprising carbon monoxide and a tracer gas; diluting concentrations of the carbon monoxide and the tracer gas in the first $D_{LCO}$ test gas with the atmospheric gas in the space resulting in a first diluted $D_{LCO}$ test gas mixture; expelling from the space the first diluted $D_{LCO}$ test gas mixture into the pulmonary diagnostic device; and confirming that the pulmonary diagnostic device reports an inspired volume consistent with the predetermined volume of first $D_{LCO}$ test gas, an alveolar volume consistent with the first maximum predetermined volume of the space, and a $D_{LCO}$ value consistent with zero diffusion.

In another exemplary embodiment, the present invention can include an apparatus for testing a pulmonary diagnostic device capable of performing single breath carbon monoxide uptake measurement, comprising: a single gas-tight chamber, with a gas port configured to receive gas from or to expel gas to the exterior of the chamber and a partition configured to change the volume of the single gas-tight chamber; the single gas-tight chamber capable of expanding and contracting; a member disposed within the single gas-tight chamber and configured to limit the movement of the partition, the member being adjustable to set a predetermined maximum volume of the single gas-tight chamber and a predetermined volume of $D_{LCO}$ test gas that the single gas-tight chamber can receive; and an interface configured for the transfer of gas between the pulmonary diagnostic device and the simulation device via the gas port.

A $D_{LCO}$ instrument will report accurate $D_{LCO}$ values if it measures inspired volume accurately and its CO and tracer gas analyzers are linear, i.e. the analyzer outputs are directly proportional to the gas concentrations. Absolute accuracy for the gas analyzers is not required. The present invention provides a method and system for confirming accurate measurement.

$D_{LCO}$ testing provides a measure for how well the lungs exchange gases with the blood across the alveolar capillary membrane. The single-breath determination of $D_{LCO}$ involves the following maneuver for the subject:

Tidal breathing, once the mouthpiece and nose clip are in place

Unforced exhalation to residual volume (RV)

Rapid inhalation (in less than 4 seconds) of the $D_{LCO}$ test gas to total lung capacity (TLC) with the inspired volume ($V_I$) as close to the know vital capacity (VC) as possible (greater than 85% VC).

Breath hold for 10+/−2 seconds

Smooth and unforced expiration exhalation in less than 4 seconds

The test gas is made up of primarily air with a small amount of CO (typically 0.3%) and a small amount of inert gas (typically helium or methane). CO has a very high affinity to the hemoglobin and is readily carried away by the blood as soon as it crosses the alveolar capillary membrane. The inert gas (also called tracer gas) is chosen for its low solubility in blood and affinity to hemoglobin. Once the test gas is inspired, the CO and tracer gas concentrations are diluted by the air in the lung prior to the inhalation. CO concentration is further reduced during the breath hold time as it diffuses into the blood.

The $D_{LCO}$ equipment records and measures the following:

Flow/volume time trace of the maneuver

CO and tracer gas concentration time traces throughout the maneuver (MacIntyre N. et. al. Standardization of the single-breath determination of carbon monoxide uptake in the lung. Eur Respir J 2005; 26: 720-73)

From the recorded time traces (data), the CO and tracer gas concentrations in the inhaled and exhaled gas samples are determined. The equipment calculates $D_{LCO}$ according to the following equation:

$$D_{LCO} = \frac{V_A}{(t/60) \times (P_B - P_{H_2O})} \ln\left(\frac{F_{I,co}/F_{A,co}}{F_{I,Tr}/F_{A,Tr}}\right) \quad \text{Eq (1)}$$

$$V_A = (V_I - V_D) \times \left(\frac{F_{I,co}/F_{A,co}}{F_{I,Tr}/F_{A,Tr}}\right) \quad \text{Eq (2)}$$

Where:

$V_A$ is the alveolar volume, expressed in mL STPD $V_D$ is the sum of the instrument dead space and subject's anatomic dead space $P_B$ is the barometric pressure and $P_{B_2O}$ the water vapor pressure in the lung $F_{I,CO}$, $F_{A,CO}$, $F_{I,Tr}$, and $F_{A,Tr}$ are concentrations of inhaled CO, alveolar CO, inhaled tracer, and alveolar tracer gases respectively The $D_{LCO}$ equipment captures the following parameters: $V_I$, $F_{I,CO}$, $F_{A,CO}$, $F_{I,Tr}$, and $F_{A,Tr}$. Both $F_{I,CO}$ and $F_{I,Tr}$ represent the concentrations of CO and tracer gas in the test gas. Typical CO and tracer gas concentrations employed by most equipment manufacturer is 3000 ppm (or 0.3%).

Inspired Volume ($V_I$):

$V_I$ is similar to vital capacity (VC) in magnitude and therefore should have a typical value ranging from around 1.5 liters (for a child) to over 6 liters (for an adult). (Hankinson, J L, Odencrantz J R, Fedan K B. Spirometric Reference Values from a Sample of the General U.S. Population Am J Respir Crit Care Med 1999; 159:179-187)

Tracer Gas Concentrations:

To estimate the range of $F_{A,Tr}$, one notes that:

$$F_{A,TR} = \frac{(V_I - V_D)}{V_A} \times F_{I,Tr} \quad \text{Eq (3a)}$$

and $$\frac{(V_I - V_D)}{V_A} \approx \frac{V_I}{V_A} \approx \frac{V_C}{TLC} = 1 - \frac{RV}{TLC} \quad \text{Eq (3b)}$$

For most subjects, the RV to TLC ratio will be between 20% and 50% (Needham C D, Rogan M C, and McDonald I. Normal Standards for Lung Volumes, Intrapulmonary Gas-Mixing, and Maximum Breathing Capacity. Thorax 1954; 9:313-325.) As a result, $F_{A,Tr}$ will be 50% to 80% of $F_{I,Tr}$ and the tracer gas analyzer must have a linear response between 50% and 100% of tracer gas concentration found in the $D_{LCO}$ test gas.

CO Concentrations:

Due to diffusion across the alveolar-capillary membrane, the ratio of alveolar CO concentration to inhaled CO concentration is lower than the corresponding ratio for the tracer gas. The effect of diffusion on alveolar CO concentration can be estimated from the $D_{LCO}$ predicted equation provided by Crapo, et. al. (Crapo R O, Morris A H, Clayton P D, and Nixon C R. Lung Volumes in Healthy Nonsmoking Adults. Bull. Europ. Physiopathol. Respir. 1982; 18:419-425):

Men: $D_{LCO}$=1.0566*Height(inches)−0.2190*Age(years)−26.34

Women: $D_{LCO}$=0.6502*Height(inches)−0.1440*Age(years)−8.36

The low limit of alveolar CO concentration will be associated with subjects with high $D_{LCO}$ values. To this end, we consider a 21-year-old male with a height of 78 inches (approximately 2 meters). Using the above-predicted equation, Eq (2), this subject will have a $D_{LCO}$ of 51.48.

Using the predicted normal equations from Crapo, this individual will likely have an alveolar volume, $V_A$(≈TLC) of 8.35 liters and VC of 6.79 liters at BTPS condition. This translates into a $V_A$ of 6.9 liters at STPD condition.

Substituting 51.48 ml/min/mm of Hg for $D_{LCO}$, 6900 mL for $V_A$, 10 seconds for t, 760 mm of Hg for $P_B$, and 47 mm of Hg for $P_{H_2O}$ in Eq(1), we obtain:

$$\ln\left(\frac{F_{I,CO}/F_{A,CO}}{F_{I,Tr}/F_{A,Tr}}\right) = \frac{51.48 \times \left(\frac{10}{60}\right) \times (760-47)}{6900} = 0.8866 \quad \text{Eq (4)}$$

or $$\frac{F_{I,CO}/F_{A,CO}}{F_{I,Tr}/F_{A,Tr}} = 2.43 \quad \text{Eq (5)}$$

$$\frac{F_{A,CO}}{F_{I,CO}} = \frac{1}{2.43} \times \frac{F_{A,Tr}}{F_{I,Tr}}$$

A high $D_{LCO}$ and therefore healthy subject will likely have a RV/TLC approaches the lower end of the range (20% to 50%). As a result, this subject will have (from Eq (3a) and Eq (3b)) a $$\frac{F_{A,CO}}{F_{I,CO}}$$

ratio of 0.8 and (from Eq (5)) a $$\frac{F_{A,CO}}{F_{I,CO}}$$

ratio of approximately 0.3. The CO gas analyzer must demonstrate a linear response between 30% and 100% of the CO gas concentration found in the $D_{LCO}$ test gas.

For quality control of $D_{LCO}$ equipment, ATS-ERS (MacIntyre N. et. al. Standardization of the single-breath determination of carbon monoxide uptake in the lung. Eur Respir J 2005; 26: 720-735) recommends performing the following:

1. Gas-analyzer zeroing: before/after each test
2. Volume (flow-sensor) accuracy: daily
3. Standard subject or simulator testing: at least weekly
4. Gas analyzer linearity: every 3 months
5. Timer accuracy: every 3 months As previously stated, the above-described embodiments and implementations are for illustration purposes only. Numerous other embodiments, implementations, and details of the invention are easily recognized by those of skill in the art from the following descriptions and claims.

BRIEF DESCRIPTION OF THE DRAWINGS

Various objects and advantages and a more complete understanding of the present invention are apparent and more readily appreciated by reference to the following Detailed Description and to the appended claims when taken in conjunction with the accompanying Drawings wherein:

DETAILED DESCRIPTION

Figure 1:
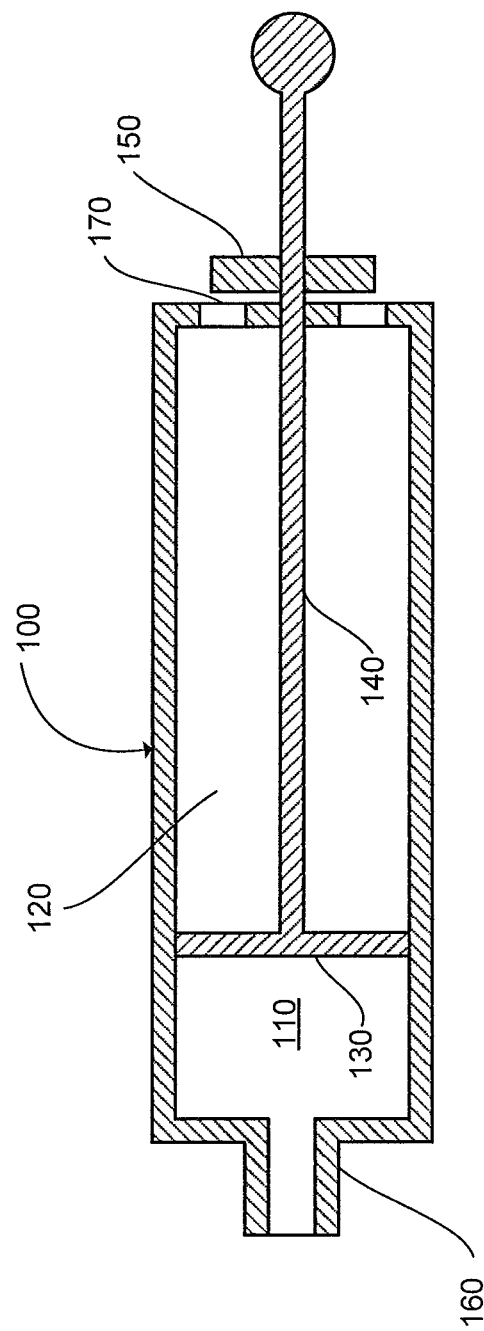
FIG. 1 illustrates an embodiment of a $D_{LCO}$ simulator.

Referring now to the drawings, where like or similar elements are designated with identical reference numerals throughout the several views, and referring in particular to FIG. 1, it illustrates the cross-section of an embodiment of a single-syringe simulator quality control device 100. The simulator syringe 100 has an inactive space 110 and a stroke volume 120 and can be a curvilinear or non-curvilinear cylinder. In a preferred embodiment, the maximum stroke volume is 6 liters or greater. Such a volume is most beneficial to simulate the inspired volumes associated with large adults. The volume of the inactive space 110 can be adjusted by moving the piston 130 either forward or back. The volume of the inactive space 110 starts from a predetermined volume. In other words, the piston 130 starts from a predetermined position. The predetermined volume can be set by a collar 150 situated on the shaft 140 of the piston 130 outside the body of the simulator syringe 100. In some embodiments, the collar 150 is adjustable so that the predetermined volume is likewise adjustable. The minimum range of adjustment of the inactive space 110 is from 20% to 70% of the total volume. Such a volume range produces alveolar gas concentrations ranging from 80% to 30% of the CO and tracer gas concentrations in the $D_{LCO}$ test gas. By adjusting the volume of the inactive space, the stroke volume is likewise adjusted. In this way, the simulated maximum predetermined volume is adjustable. Vent holes 170 ensure that the piston 130 can move freely throughout the stroke volume 120 by maintaining the pressure behind the piston close to that of the ambient condition.

The piston 130 can have different thicknesses and can be composed of different materials. In some embodiments, the piston 130 can make full contact with the inner wall of the simulator syringe 100 such as to create a hermetic seal between the inactive space 110 and the stroke volume 120.

Figure 2:
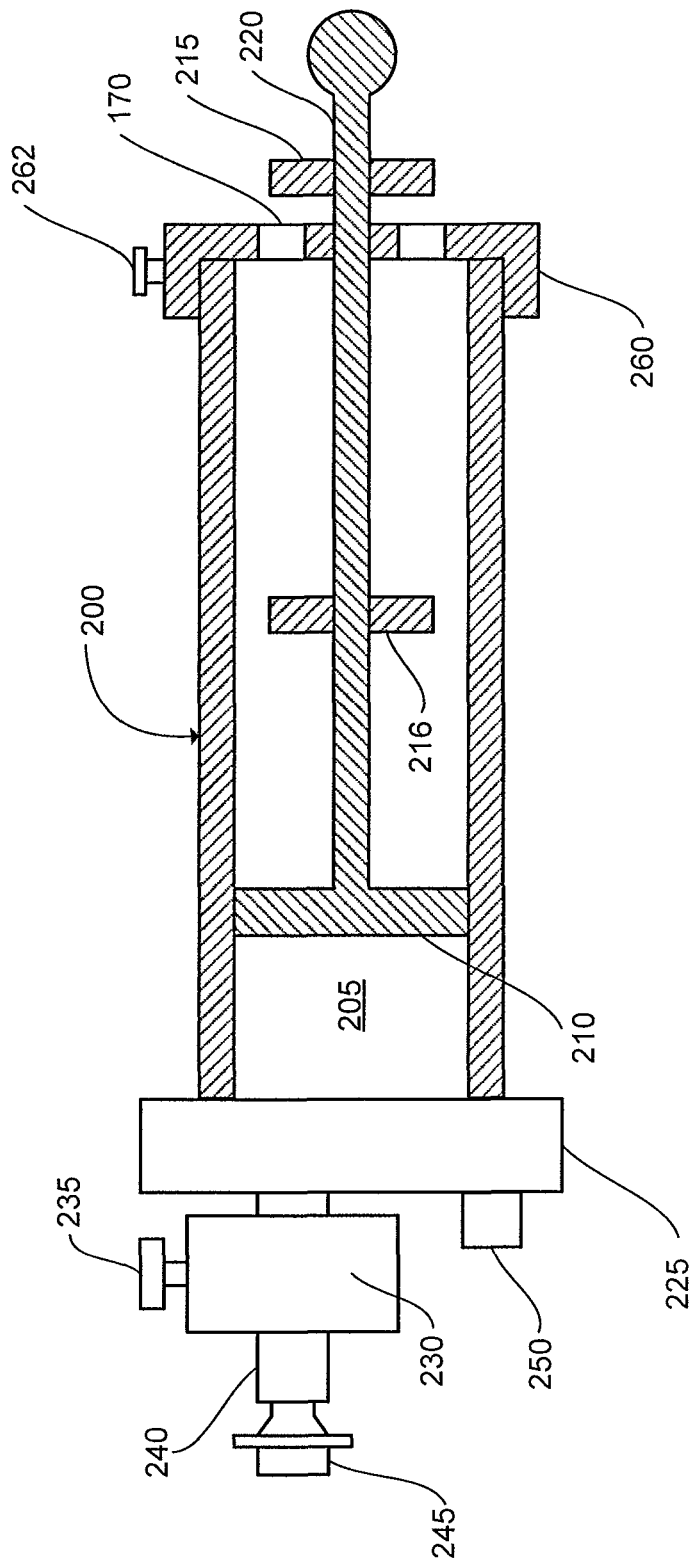
FIG. 2 illustrates an embodiment of a $D_{LCO}$ simulator

Referring now to FIG. 2, an illustration of a simulator with a cut-away view of a simulator syringe 200 is shown. In the embodiment shown, adjustable stop 215 is external to the simulator syringe and adjustable stop 216 is disposed in the interior of the simulator syringe 200. Placement of the stop 215 can be adjusted to determine the starting volume of the inactive space whereas the placement of the stop 216 can be adjusted to determine the maximum volume of the inactive space. In a preferred embodiment, the stop 215 and stop 216 are adjustable so that the starting volume of the inactive space 205 and the maximum volume of the inactive space 205 can be determined by placement of the stop 215 and stop 216. The adjustable stop 215 can be adjusted from outside the body of the simulator syringe 200. Similarly, the adjustable stop 216 can be adjusted by removing the positioning cap 260 by first loosening up the locking screw 262. In other embodiments, a stop can be situated either internal, external, or both to the body of the simulator syringe 200 can be used to determine the starting and maximum volumes of the inactive space 205.

The simulator syringe 200 also includes an end cap 225. Within the end cap 225 is a fan for priming the inactive space 205 with atmospheric air. A battery pack 250 is used to power the fan. In other embodiments, the fan can be powered by some other DC or AC power source or can be manually powered. End caps similar to end cap 225 are discussed in more detail below. Attached to the end cap 225 is valve 230 with valve handle 235. Valve 230 can be used to isolate the simulator syringe 200 and the inactive space 205 from the $D_{LCO}$ equipment. This can be useful to simulate a breath hold during a test. It should be understood that other embodiments will lack a valve 230.

Attached to exhaust tube 240 is the mouth-piece end 245 (i.e., gas port). In some embodiments, the end 245 of the simulator can be a shaped end that fits onto a mouthpiece of the $D_{LCO}$ equipment to be tested or calibrated. Such shaped ends can be customized based on the particular $D_{LCO}$ equipment. In other embodiments, the end 245 can be a normal end of the syringe, the end 245 not intended to fit snuggly onto or into the mouthpiece or mask of the $D_{LCO}$ equipment. In yet other embodiments, the end 245 can include an end cap as illustrated in FIGS. 4-8 and discussed below. It is to be understood that the configuration of components attached to end cap 245 is not meant to be limiting. Other embodiments can include a subset of these components, additional components, and different configurations of components. The combined volume of those portions of the simulator device between the syringe volume of the diagnostic device represent the analog of the anatomical dead space (i.e., mouth, trachea, etc.) of a patient/subject.

Figure 3:
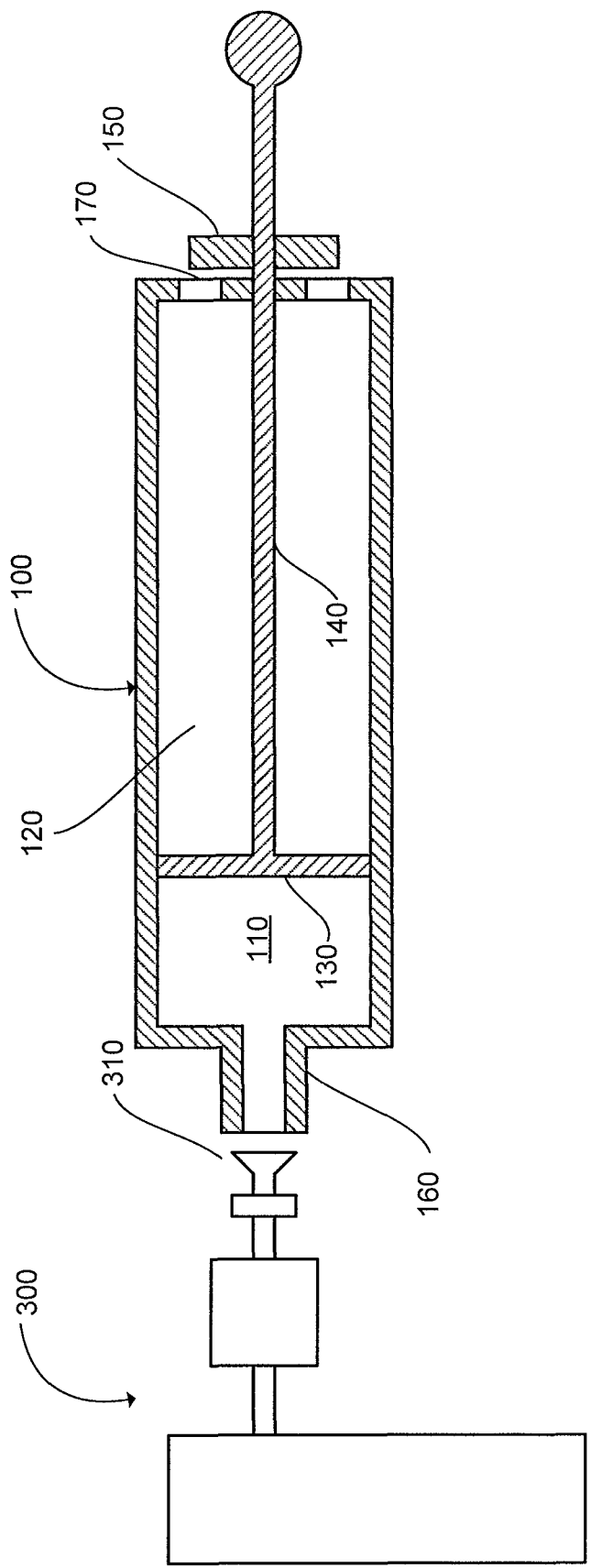
FIG. 3 illustrates a portion of an embodiment of a system that includes a $D_{LCO}$ testing device and a $D_{LCO}$ simulator.

Referring now to FIG. 3, an embodiment of at least part of a system of $D_{LCO}$ equipment 300 and a simulator 100 is shown. In the embodiment shown, the simulator 100 has a generic end 160 (i.e., gas port) for communicating with the $D_{LCO}$ equipment 300 and its mouthpiece 310. As discussed above, the simulator syringe 100 can have a custom end to fit the particular $D_{LCO}$ equipment 300 or and end cap. It should be understood that $D_{LCO}$ simulators in accordance with the present invention can be used with different types of $D_{LCO}$ equipment and that the invention is not limited to any particular type of $D_{LCO}$ equipment.

Figure 4:
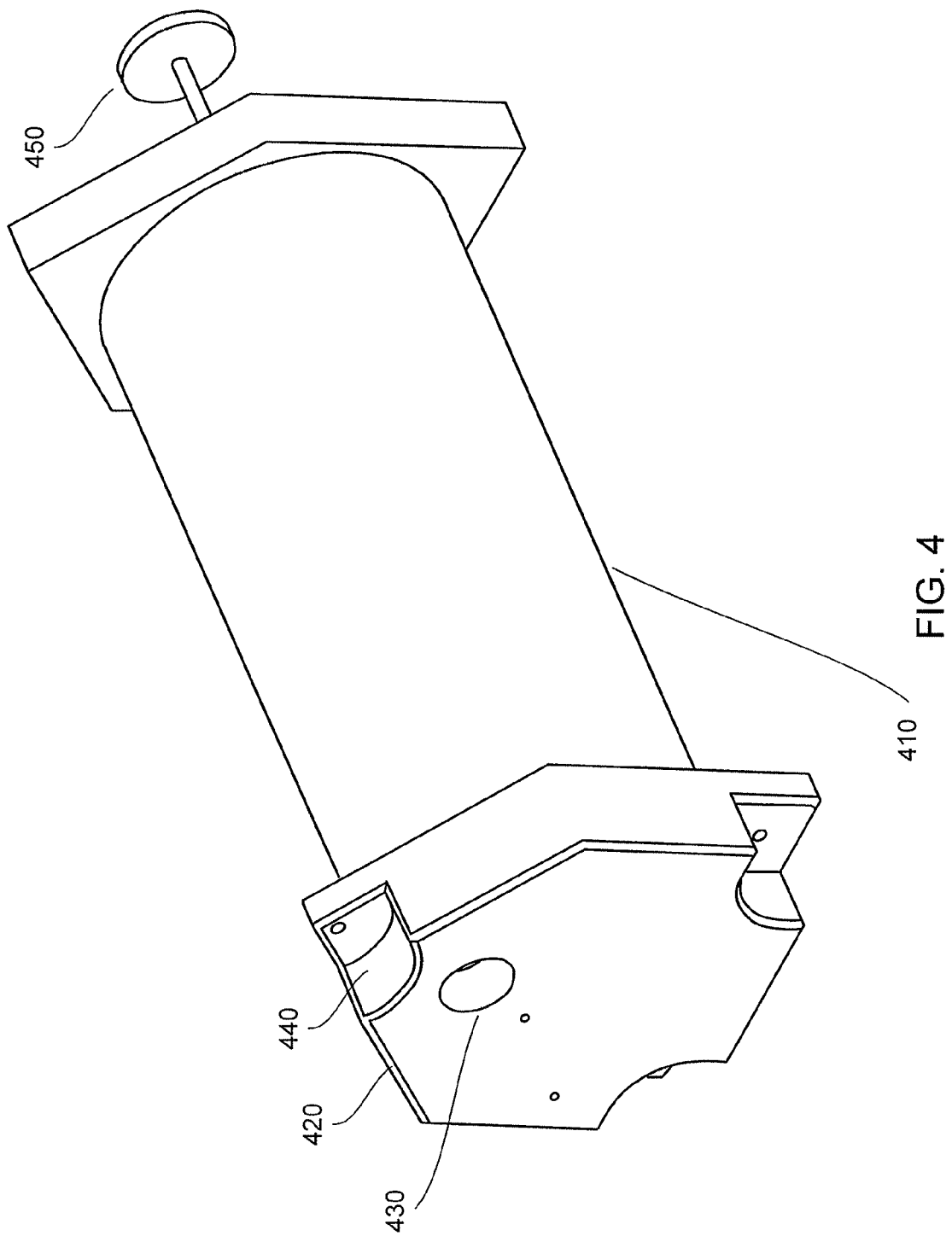
FIG. 4 illustrates a view of a $D_{LCO}$ simulator.

FIG. 4 shows an embodiment of a simulator syringe 410 that includes an end cap 420. The simulator syringe 410 also includes a plunger 450 for the piston internal to the simulator syringe 410. The end cap 420 shown serves as a manifold to connect the simulator syringe 410 to a $D_{LCO}$ equipment connector, which is not shown. The $D_{LCO}$ equipment connector enables communication between the simulator and the $D_{LCO}$ equipment and is similar to the end 225 described above. The hole 430 of the end cap 420 receives the $D_{LCO}$ equipment connector. In the embodiment shown, the grooves 440 allow access to fasteners used to attach end cap 420 to the simulator syringe 410.

Figure 5:
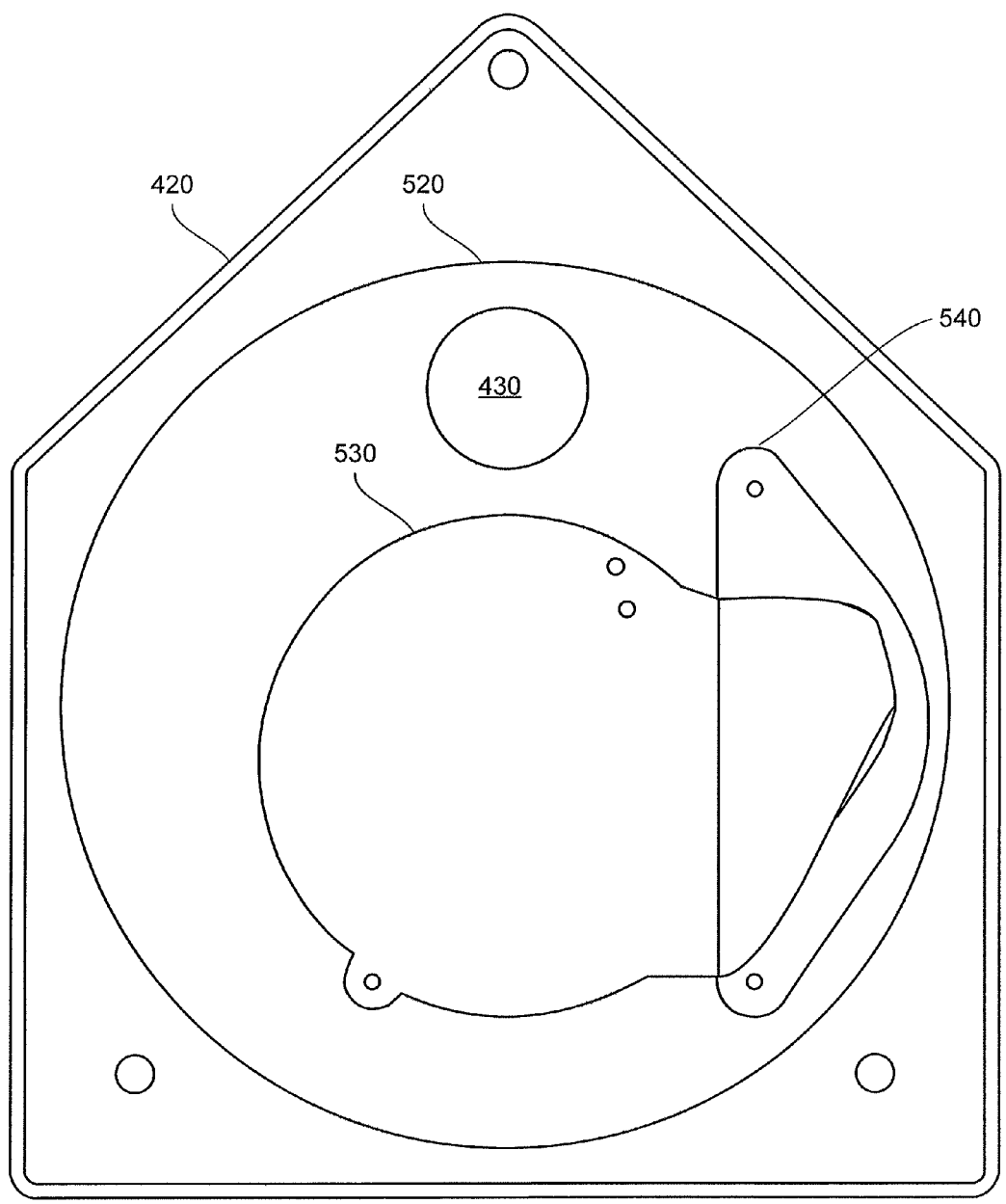
FIGS. 5-8 illustrate views of an end cap of a $D_{LCO}$ simulator.

Referring now to FIG. 5, a schematic of the end cap 420 is shown. The cavity 530 can be used to house a fan or blower to promote gas mixing in the inactive space 110, 205. Cavity 540 can be used to house a plate with exhaust for the fan or blower. Those of skill in the art can appreciate other arrangements for a fan or blower and an exhaust. For example, in other embodiments, a fan can be placed directly on the body of the simulator syringe. The connector hole 430 allows for the $D_{LCO}$ equipment connector to communicate with the simulator syringe. Cavity 520 can include threading to screw the end cap 420 onto the body of the simulator syringe.

Figure 6:
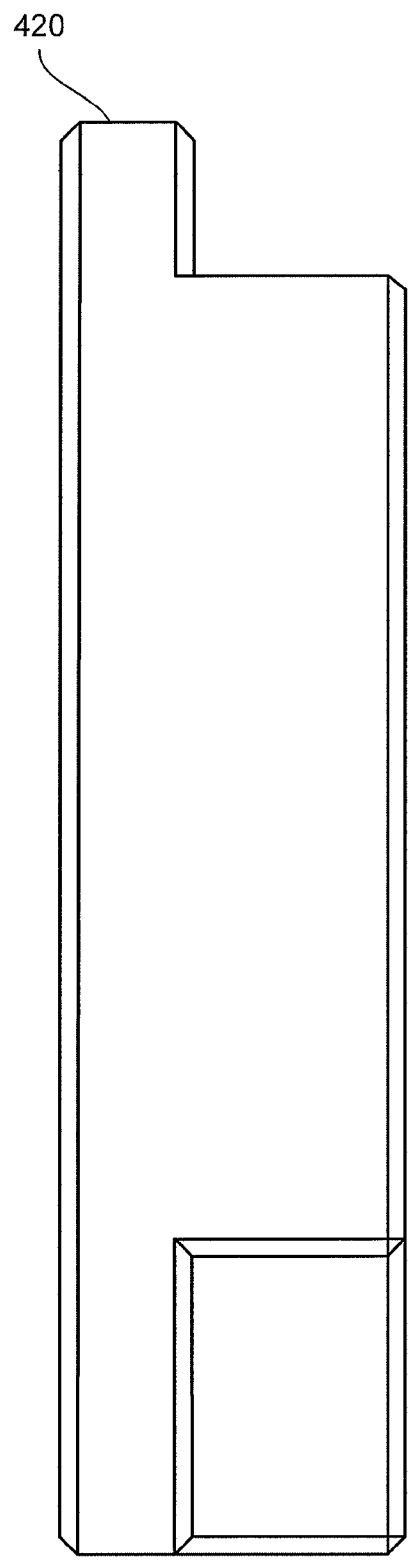
Figure 7:
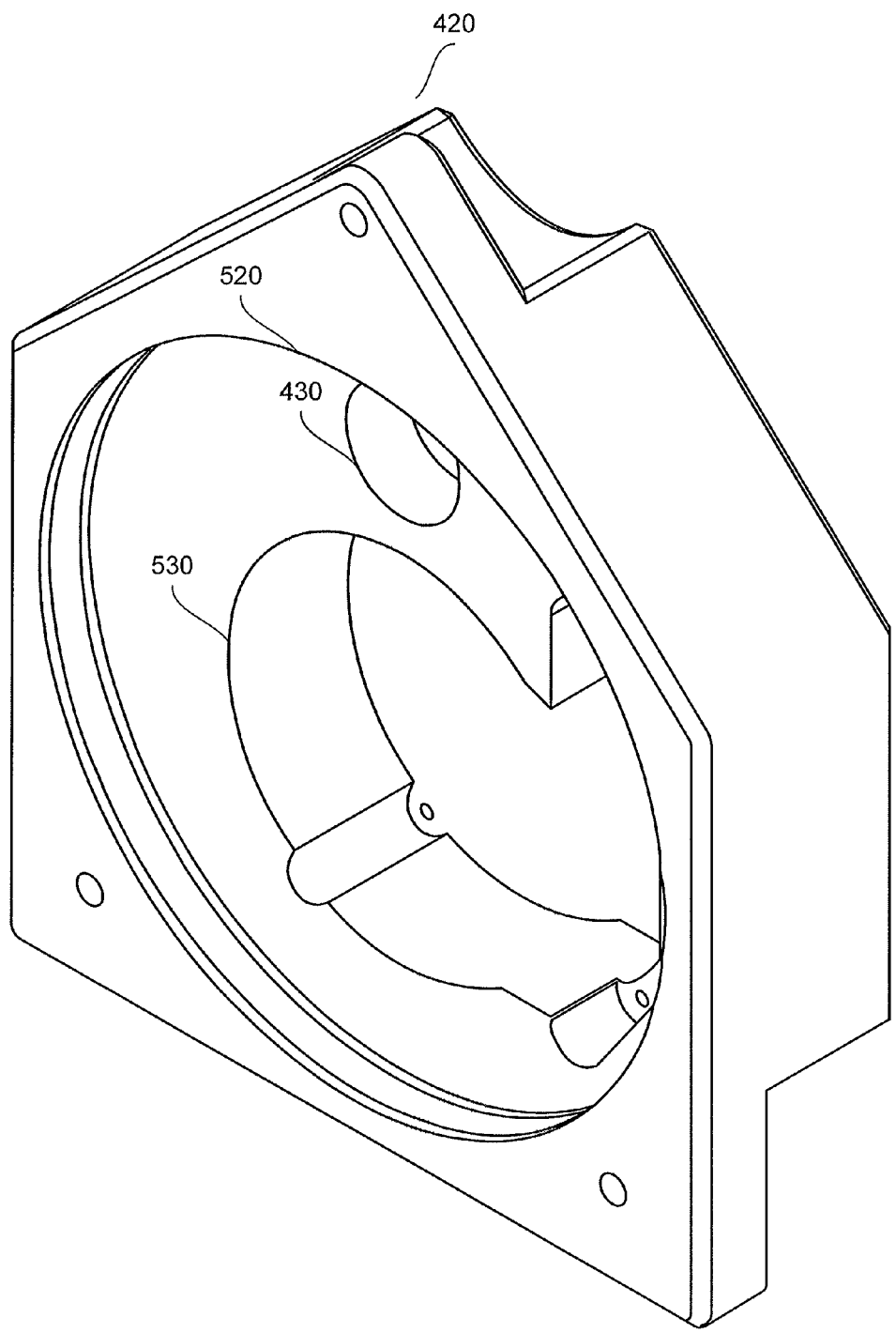
Figure 8:
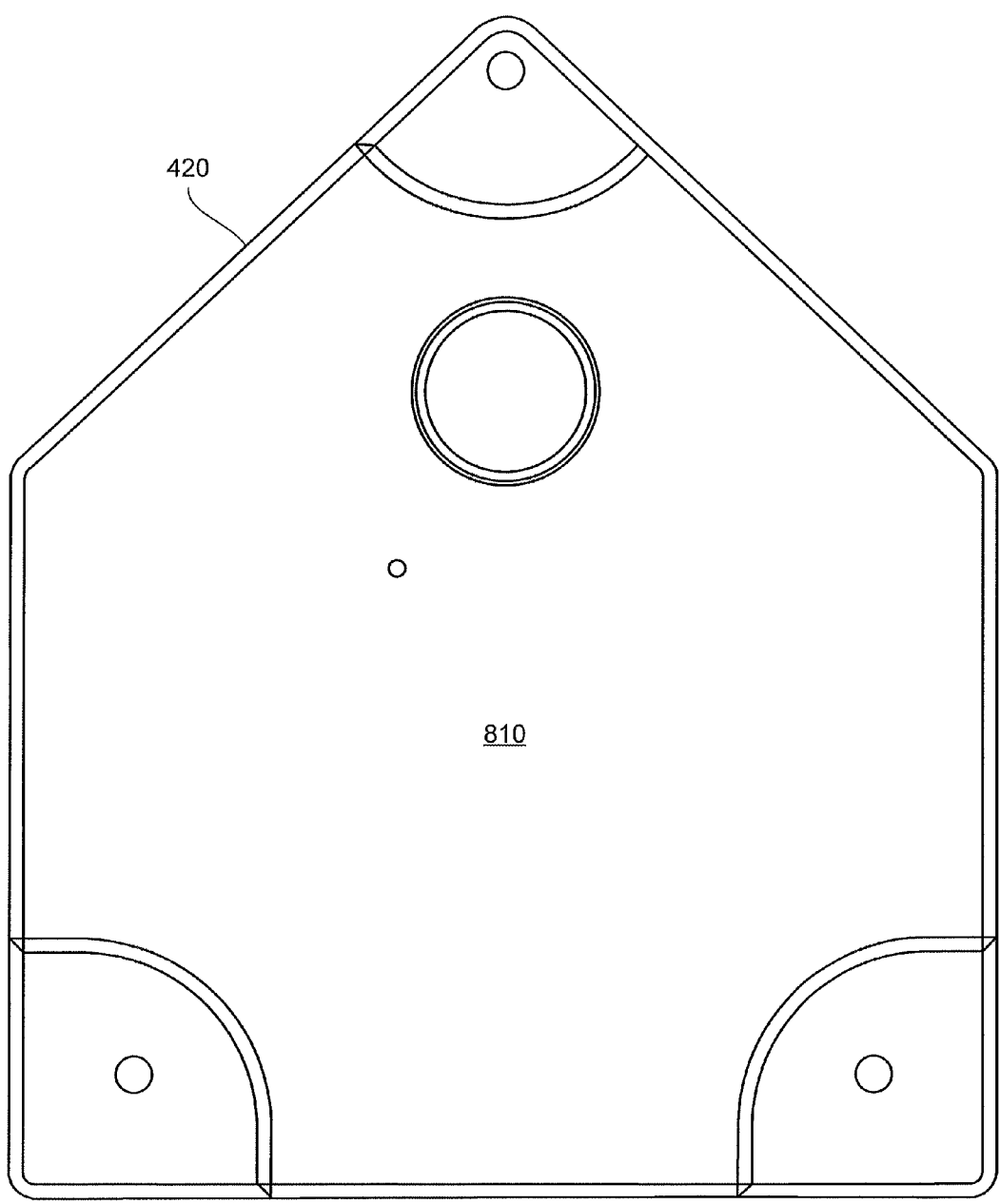

FIG. 6 includes a side view of the end cap 420 as described above and shown in FIG. 5. In FIG. 7, a three-quarter view of the end cap 420 as described above and shown in FIGS. 5-6 is shown. In FIG. 8, the front view of the end cap 420 as described above and shown in FIGS. 5-7 is shown. The illustration of end cap 420 of FIG. 8 includes a cover 810 over the cavities (520, 530, 540) as shown in FIGS. 5 and 7.

Figure 9:
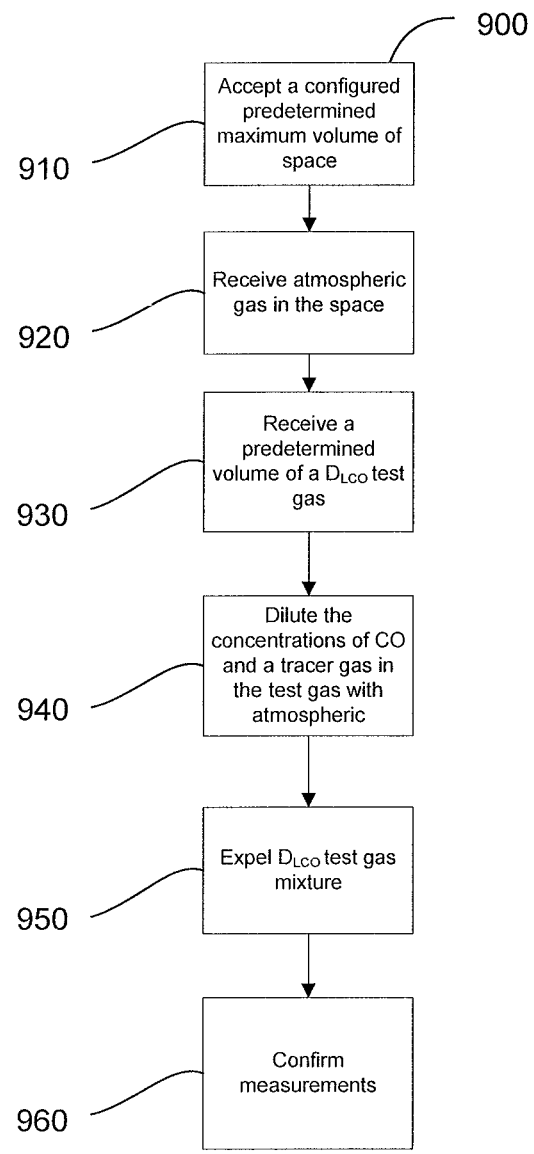
FIGS. 9-10 are flowcharts of method for quality control of $D_{LCO}$ equipment.

Referring now to FIG. 9 is a flowchart depicting a method 900 for testing $D_{LCO}$ equipment. At step 910, a predetermined maximum volume of space is configured. In a preferred embodiment, a collar is set at a point along a longitudinal axis of the syringe cylinder so that the syringe piston cannot move beyond the collar during the simulation of inspiration. In other embodiments, a maximum volume can be configured by setting a some other rigid portion of the simulator device at which a wall or boundary of the space cannot be moved past. Such a rigid portion can include an adjustable external wall or wall portion that the boundary of the space expands to. At step 920, atmospheric gas is received in the space. At this step 920, the simulator is primed so that an initial inactive space within the simulator contains atmospheric gases that would also be present in the lungs of a patient using the $D_{LCO}$ equipment. In a preferred embodiment, priming the simulator so that atmospheric gas is properly received can be accomplished by a piston moving in a reciprocating motion, by creating a vacuum or partial vacuum within the space, by mechanically introducing atmospheric gas by a fan or blower, and the like.

At step 930, a predetermined volume of a $D_{LCO}$ test gas is received. In a preferred embodiment, the $D_{LCO}$ test gas contains at least carbon monoxide and a tracer gas and will be received from the diagnostic device. In such a case, the same test gas cartridge or other container that is typically used during an actual diagnosis with a patient or subject is also used for the simulation. Further, in a preferred embodiment using a syringe, the volume in the syringe is increased to the predetermined maximum volume.

In some embodiments, a piston is pulled back to a predefined stop location. In other embodiments, other mechanisms for expanding the volume to a predetermined volume can be used. For example, the volumes in other embodiments can be other types of curvilinear volumes, for example spheroid, elliptical cylinder, conical cylinder, cone, etc., or non-curvilinear volumes, for example a cube with one or more expanding sides. In yet other embodiments, volume can be expanded by virtue of some elasticity in one or more facets of the simulator. The elasticity can be limited or have predefined extents. Accordingly, other sides of the volume can be expanded out to increase the volume. In preferred embodiments, the total volume of the simulator is constant and known. In embodiments in which a syringe or other type of dual-chamber configuration is used, the total volume of the inactive space and stroke volume is constant and known. Further, in a preferred embodiment, receiving the test gas should simulate exhalation in a diagnostic setting and last 4 seconds or less.

During an actual test of a patient or subject, at the end of a maximal inhalation, the gas volume in the lung is the total lung capacity, or alveolar volume. In a preferred embodiment, when the piston is pulled all the way back or the volume of the space otherwise reaches the predetermined maximum, the gas volume inside the space is the sum of the volume corresponding to piston displacement or the volume increase of the space (analogous to the inspired volume in the case of a patient/subject) and the volume of the inactive space (analogous to the residual volume in the patient/human). Therefore, a simulator will always have the same "Total Lung Capacity or Alveolar Volume" regardless of the initial inactive space.

At step 940, the concentrations of carbon monoxide and the tracer gas from the test gas are diluted. Here, those concentrations can mix with the atmospheric gas to create a test gas concentration. In some embodiments, the dilution can be accomplished or assisted by way of convection or diffusion. For example, the gases in the space can be exposed to a fan that provide convective flow within the space, thereby causing the gases to mix and the test gas concentrations to become diluted and more uniform throughout the interior of the syringe volume. In another embodiment, vanes at or near the inlet port of the syringe can redirect the flow of the gas as the syringe piston is pulled back thereby causing gas swirls within the interior of the syringe and resulting in enhanced mixing of the test gas and the atmospheric gas. While in other embodiments, diffusing the gas concentrations can be accomplished by pausing for a predetermined amount of time before expelling the test gas mixture, thus allowing the test gas concentrations to naturally diffuse. The predetermined time is optimally at least 10 seconds. At step 950, the $D_{LCO}$ test gas mixture is expelled. In a preferred embodiment, the expulsion is accomplished by decreasing the volume of the space. The $D_{LCO}$ test gas mixture is expelled to the pulmonary diagnostic equipment for testing. In a preferred embodiment, the expulsion should simulate exhalation and last 4 seconds or less.

During an actual test of a patient or subject, at the end of a maximal exhalation, the gas volume in the lung is the residual volume. In a preferred embodiment, when the test gas is expelled, via pushing the piston all the way in or by otherwise reducing the volume of the space, the gas volume left inside the syringe is the inactive space.

At step 960, measurements from the pulmonary diagnostic device are confirmed. In a preferred embodiment, the method is designed to produce the following results for a properly functioning $D_{LCO}$ device, regardless of the predetermined maximum volume:

Measured alveolar volume equal to the predetermined maximum volume, within the error specifications of the pulmonary diagnostic $D_{LCO}$ device and reported under the same conditions (e.g. BTPS or STPD)

Measured $D_{LCO}$ value of zero, within the error specifications of the pulmonary diagnostic $D_{LCO}$ device The relationship between alveolar volume, inspired volume, dead space volume, inspired tracer gas concentration and alveolar tracer gas concentration is provided by:

$$V_A = (V_I - V_D) \times \left(\frac{F_{I,Tr}}{F_{A,Tr}}\right)$$

When $D_{LCO}$ testing is performed on a patient, $V_D$ is the sum of the $D_{LCO}$ equipment patient interface dead space and the patient's anatomical dead space (generally equal to 2.2 mL per kg of patient's weight). When testing is performed with the syringe simulator, the volume of the coupling between the $D_{LCO}$ equipment patient interface and the syringe will replace the anatomical dead space.

As the inactive space increases (by varying the collar position on the shaft of the syringe), both the inspired volume and $F_{A,Tr}$ decrease and in such a manner that the reported alveolar volume remains constant, if the tracer gas analyzer is linear throughout its intended range of operation. Errors in the alveolar volume (i.e. deviation from the expected value) are a good representation of the linearization error of the tracer gas analyzer.

Since CO is diluted in exactly the way as the tracer gas by the gas in the inactive volume, the ratios $F_{I,CO}/F_{A,CO}$ and $F_{I,Tr}/F_{A,Tr}$ should be identical. As a result, $$\ln\left(\frac{F_{I,CO}/F_{A,CO}}{F_{I,Tr}/F_{A,Tr}}\right) = \ln(1) = 0 \quad \text{(Eq (2))}$$

and according to Eq (1) the reported $D_{LCO}$ values should remain near 0 as the inactive space increases and alveolar CO and tracer gas concentrations decrease. Slight deviations from 0 are a good representation of overall accuracy of the $D_{LCO}$ equipment.

It is important to note that $D_{LCO}$ values will be zero if the ratios $F_{I,CO}/F_{A,CO}$ and $F_{I,Tr}/F_{A,Tr}$ are identical. The two values are identical when both analyzers have similar/identical response characteristics to concentrations. However, zero $D_{LCO}$ values during testing of the equipment with a syringe alone do not guarantee that the gas (CO and tracer) analyzers are linear, as recommended by ATS/ERS.

The combination of constant alveolar volume and zero $D_{LCO}$ values ensures: (1) the tracer gas analyzer is linear and (2) the CO gas and tracer gas analyzers have identical linearity characteristics. Hence, the CO gas analyzer must also be linear.

To properly verify its performance, $D_{LCO}$ equipment should be tested at different combinations of inspired volumes, CO gas concentrations, and tracer gas concentrations corresponding to conditions encountered in subject testing.

With the collar set on the 1 liter mark, the inspire volume ($V_I$) should be 6 liters (ATPD)+/−3% or better, when a 7 liter simulator syringe is employed. Note: the $D_{LCO}$ device may report $V_I$ at BTPS. Appropriate conversion must be performed prior to comparison with the expected values. Similarly with the collar set on 2, 3, 4, and 5 liter marks, the $V_I$ should be 5, 4, 3, and 2 liters respectively. The alveolar volume ($V_A$) should be within 5% or better of the total internal volume of the simulator (syringe) for a $D_{LCO}$ equipment in reasonable condition. Note: the $D_{LCO}$ device may report $V_A$ at BTPS or STPD. Appropriate conversion must be performed prior to comparison with the expected value. The $D_{LCO}$ values should be less than 2 mL/min/mm of Hg. The simulator should be checked for leak as well if $D_{LCO}$ values are higher than expected for all collar positions.

Figure 10:
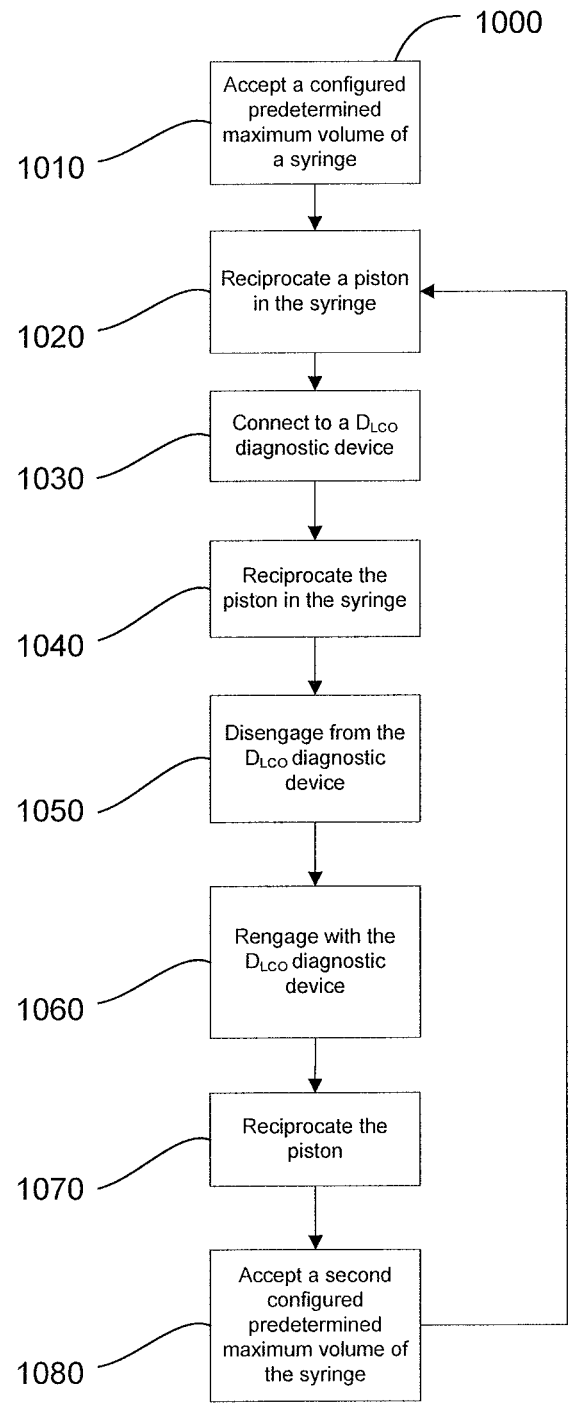

Referring now to FIG. 10, a flowchart for a method 1000 in accordance with the present invention is shown. At step 1010, a configured predetermined maximum volume of a syringe is accepted. In a preferred embodiment, a collar is adjusted so that a piston in the syringe is stopped at a point where a particular maximum volume is reached. In one embodiment, an optimal maximum volume is at least 1 liter and no more than 7 liters. At step 1020, the piston of the syringe is reciprocated. In a preferred embodiment, reciprocation of the piston is accomplished via a plunger and the result is the syringe becomes filled with the ambient air.

At step 1030, the syringe is connected to a $D_{LCO}$ diagnostic device. In a preferred embodiment, the syringe includes an end cap that attaches to the mouthpiece or other patient interface of the $D_{LCO}$ diagnostic device. At step 1040, the piston is reciprocated again. Reciprocation of the piston simulates tidal breathing of a patient/subject. In a preferred embodiment, the piston is reciprocated so that each reciprocation displaces between 0.5 liters and 1 liter, in the simulation of maximal exhalation, the piston is pushed all the way in, and in the simulation of maximal inhalation, the piston is pulled out rapidly. As a result of the maximal inhalation, test gas from the $D_{LCO}$ diagnostic device is received by the syringe.

At step 1050, the syringe is disengaged from the $D_{LCO}$ diagnostic device. In a preferred embodiment, a valve can be closed to separate the syringe space from the $D_{LCO}$ diagnostic device and the syringe is disengaged for approximately 10 seconds. At step 1060, the syringe is reengaged with the $D_{LCO}$ diagnostic device. In a preferred embodiment, a valve can be opened to remove a separation between the syringe space and the $D_{LCO}$ diagnostic device. In other embodiments, steps 1030 and 1050 can be accomplished by removing the simulator syringe from the $D_{LCO}$ diagnostic device to actuate a member that seals the end of the simulator syringe. Those of skill in the art can appreciate that the disengagement can be accomplished by other mechanisms.

At step 1060, the syringe is reengaged with the $D_{LCO}$ diagnostic device. At step 1070, the piston is reciprocated. In preferred embodiment, the piston is pushed in to expel test gas from the simulator syringe to the $D_{LCO}$ diagnostic device for measurement. At step 1080, a second configured predetermined maximum volume of the syringe is accepted. In a preferred embodiment, the second configured predetermined maximum volume is different that the configured predetermined maximum volume at step 1010. And the second configured predetermined maximum volume can be set in accordance with embodiments described herein. In a preferred embodiment steps 1020 through 1070 are repeated. In this way, the accuracy of the $D_{LCO}$ diagnostic device's measurements can be verified. In a preferred embodiment, the steps are repeated with configured predetermined volumes set so that the inactive space of the simulator syringe ranges from 1 to 5 liters at 1 liter intervals.

In conclusion, the present invention provides, among other things, a system and method for the quality control of $D_{LCO}$ equipment. Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions fall within the scope and spirit of the disclosed invention as expressed in the claims.

What is claimed is:

1. A method for testing a pulmonary diagnostic device comprising:
   receiving a simulated dead volume of atmospheric gas into a test device;
   receiving a simulated inspired volume of $D_{LCO}$ test gas from the pulmonary diagnostic device, the test gas including a first concentration of carbon monoxide and a first concentration of a tracer gas, the simulated inspired volume and the simulated dead volume collectively defining a simulated alveolar volume, the simulated inspired volume received into test device while the test device contains the simulated dead volume such that the simulated inspired volume of $D_{LCO}$ test gas is diluted by the simulated dead volume of atmospheric gas to produce a simulated alveolar volume of diluted $D_{LCO}$ test gas, the diluted $D_{LCO}$ test gas having a second concentration of carbon monoxide and a second concentration of tracer gas; and
   expelling the simulated inspired volume of diluted $D_{LCO}$ test gas from the test device into the pulmonary diagnostic device such that the pulmonary diagnostic device reports an inspired volume consistent with the simulated inspired volume, an alveolar volume consistent with the simulated alveolar volume, and a $D_{LCO}$ value consistent with zero diffusion.

2. The method of claim 1, wherein the simulated inspired volume is a first simulated inspired volume of a first $D_{LCO}$ test gas, the inspired volume is a first inspired volume, and the $D_{LCO}$ value is a first $D_{LCO}$ value, the method further comprising:
   receiving a second simulated inspired volume of a second $D_{LCO}$ test gas from the pulmonary diagnostic device the second $D_{LCO}$ test gas including a third concentration of carbon monoxide and a third concentration of tracer gas;
   diluting the second simulated inspired volume of the second $D_{LCO}$ test gas with a volume of atmospheric gas, the volume of atmospheric gas and the second simulated inspired volume collectively defining a second simulated alveolar volume of a second diluted $D_{LCO}$ test gas;
   expelling the second simulated inspired volume of the second diluted $D_{LCO}$ test gas from the test device into the pulmonary diagnostic device such that the pulmonary diagnostic device reports a second inspired volume consistent with the second simulated inspired volume and a second $D_{LCO}$ value consistent with zero diffusion.

3. The method of claim 1, wherein the simulated dead volume is a first simulated dead volume, the simulated inspired volume is a first simulated inspired volume, the inspired volume is a first inspired volume, and the $D_{LCO}$ value is a first $D_{LCO}$ value, the method further comprising:
   receiving a second simulated dead volume of atmospheric as into a test device the second simulated dead volume different from the first simulated dead volume;
   diluting a second simulated inspired volume of the $D_{LCO}$ test gas with the second simulated dead volume of atmospheric gas to produce a second diluted $D_{LCO}$ test gas, the second simulated inspired volume different from the first simulated inspired volume, the second simulated inspired volume and the second dead volume collectively defining the simulated alveolar volume, the second diluted $D_{LCO}$ test gas having a fourth concentration of carbon monoxide and a fourth concentration of tracer gas;

expelling the second simulated inspired volume of the second diluted $D_{LCO}$ test gas from the test device into the pulmonary diagnostic device such that the pulmonary diagnostic device reports a second inspired volume consistent with the second simulated inspired volume, the alveolar volume, and a second $D_{LCO}$ value consistent with zero diffusion.

4. The method of claim 1, further comprising convecting the simulated inspired volume of $D_{LCO}$ test gas and the simulated dead volume of atmospheric gas.

5. The method of claim 1, wherein the simulated inspired volume of $D_{LCO}$ test gas is diffused into the simulated dead volume of atmospheric gas.

6. The method of claim 1, wherein the simulated inspired volume of diluted $D_{LCO}$ test gas is expelled such that the pulmonary diagnostic device reports zero diffusion.

7. A method, comprising:
reciprocating a piston of a cylinder in the presence of atmospheric gas such that the simulated dead volume contains atmospheric gas;
drawing a simulated inspired volume of $D_{LCO}$ test gas into the cylinder, the $D_{LCO}$ test gas including a first concentration of carbon monoxide and a first concentration of tracer gas;
mixing the simulated dead volume of atmospheric gas and the simulated inspired volume of $D_{LCO}$ test gas to produce the simulated alveolar volume of a mixed gas, the mixed gas having a second concentration of carbon monoxide and a second concentration of tracer gas; and
expelling the simulated inspired volume of the mixed gas into a pulmonary diagnostic device such that the pulmonary diagnostic device reports a $D_{LCO}$ value of zero based on a ratio of the first concentration of carbon monoxide to the second concentration of carbon monoxide equaling a ratio of the first concentration of the tracer gas to the second concentration of the tracer gas, plus or minus a value representative of the accuracy of the pulmonary diagnostic device.

8. The method of claim 7 wherein the simulated inspired volume of the mixed gas is expelled into the pulmonary diagnostic device such that the pulmonary diagnostic device reports an alveolar volume consistent with the simulated alveolar volume and a inspired volume consistent with the simulated inspired volume.

9. The method of claim 7, wherein the pulmonary diagnostic device reports a $D_{LCO}$ value of greater than 2 mL/min/mm of Hg, the method further comprising:

trouble shooting the pulmonary diagnostic device based on the $D_{LCO}$ value being greater than 2 mL/min/mm of Hg.

10. The method of claim 7, wherein the mixing includes the simulated dead volume of atmospheric gas and the simulated inspired volume of $D_{LCO}$ test gas diffusing to produce the simulated alveolar volume of a mixed gas.

11. The method of claim 8, further comprising:
setting a stop position of the piston before reciprocating the piston, the piston and the cylinder collectively defining the simulated dead volume when the piston is disposed against the stop position.

12. The method of claim 8, wherein the simulated dead volume is a first simulated dead volume, the simulated inspired volume is a first simulated inspired volume, the $D_{LCO}$ test gas is a first $D_{LCO}$ test gas, the mixed gas is a first mixed gas, and the $D_{LCO}$ value is a first $D_{LCO}$ value, the method further comprising:
reciprocating the piston in the presence of atmospheric gas such that a second simulated dead volume contains atmospheric gas, the second simulated dead volume different from the first simulated dead volume;
drawing a second simulated inspired volume of a second $D_{LCO}$ test gas into the cylinder, the second simulated inspired volume different from the first simulated inspired volume, the second $D_{LCO}$ test gas having a third concentration of carbon monoxide and a third concentration of tracer gas;
mixing the second simulated dead volume of atmospheric gas and the second simulated inspired volume of the second $D_{LCO}$ test gas to produce the simulated alveolar volume of a second mixed gas, the second mixed gas having a fourth concentration of carbon monoxide and a fourth concentration of tracer gas; and
expelling the second simulated inspired volume of the second mixed gas such that the pulmonary diagnostic device reports a second $D_{LCO}$ value of zero based on a ratio of the third concentration of carbon monoxide to the fourth concentration of carbon monoxide of the expelled gas equaling a ratio of the third concentration of the tracer gas to the fourth concentration of the tracer gas plus or minus a value representative of the accuracy of the pulmonary diagnostic device.

13. The method of claim 12, further comprising:
correcting a linearization error of the pulmonary diagnostic device based on a difference between the first $D_{LCO}$ value and the second $D_{LCO}$ value.

* * * * *